(12) United States Patent
Ting et al.

(10) Patent No.: US 6,426,759 B1
(45) Date of Patent: *Jul. 30, 2002

(54) APPARATUS AND METHOD FOR MANAGING CHANGES OF COMPUTERIZED MEDICAL PROTOCOLS

(75) Inventors: Annsheng C. Ting, Los Altos Hills; Kenneth I. Macrae, Atherton; Chung-Jen Ho, Los Altos; Mark Steven Schroeder, Belmont; Michael Aaron Thompson, Milpitas, all of CA (US)

(73) Assignee: Confer Software, Inc., San Carlos, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/388,259

(22) Filed: Sep. 1, 1999

Related U.S. Application Data

(63) Continuation-in-part of application No. 09/153,829, filed on Sep. 15, 1998, now Pat. No. 6,037,940, which is a continuation-in-part of application No. 08/546,212, filed on Oct. 20, 1995, now Pat. No. 5,850,221, which is a continuation-in-part of application No. 08/546,213, filed on Oct. 20, 1995, now Pat. No. 5,826,237.

(51) Int. Cl.[7] .............................................. G06K 15/00
(52) U.S. Cl. ...................................... 345/763; 345/855
(58) Field of Search ............................... 345/348, 349, 345/352–355, 356–357, 340, 339, 854, 838–839, 763, 772, 712, 713, 805, 825, 835, 840, 855, 861; 705/3; 707/10, 11

(56) References Cited

U.S. PATENT DOCUMENTS

| | | | |
|---|---|---|---|
| 4,525,885 A | 7/1985 | Hunt et al. ..................... 5/453 |
| 4,842,394 A | 6/1989 | Buchroeder ................. 350/432 |
| 5,090,648 A | 2/1992 | Wood et al. ................. 248/125 |
| 5,208,748 A | 5/1993 | Flores et al. ................. 364/419 |
| 5,216,603 A | 6/1993 | Flores et al. ................. 364/419 |
| 5,243,531 A | 9/1993 | DiPippo et al. ............. 364/468 |
| 5,253,164 A | 10/1993 | Holloway et al. .......... 364/406 |
| 5,301,301 A | 4/1994 | Kodosky et al. ............ 395/500 |
| 5,408,603 A * | 4/1995 | Van de Lavoir et al. ... 345/348 |
| 5,412,804 A | 5/1995 | Krishna ....................... 395/600 |
| 5,428,734 A * | 6/1995 | Haynes et al. ............... 345/348 |
| 5,734,915 A * | 3/1998 | Roewer ....................... 345/773 |
| 5,772,585 A * | 6/1998 | Lavin et al. ................. 600/300 |
| 5,786,816 A | 7/1998 | Macrae et al. .............. 345/339 |
| 5,826,237 A | 10/1998 | Macrae et al. .................. 705/2 |
| 5,850,221 A | 12/1998 | Macrae et al. .............. 345/348 |
| 5,886,693 A | 3/1999 | Ho et al. ..................... 345/335 |
| 5,924,074 A * | 7/1999 | Evans ............................ 705/3 |
| 5,930,803 A * | 7/1999 | Becker et al. .............. 707/104 |
| 5,946,659 A | 8/1999 | Lancelot et al. ............... 705/3 |
| 5,950,630 A | 9/1999 | Portwood et al. ........... 128/897 |
| 5,953,704 A | 9/1999 | McIlroy et al. ................ 705/2 |
| 5,960,403 A | 9/1999 | Brown .......................... 705/2 |
| 6,026,363 A * | 2/2000 | Shepard ........................ 705/3 |
| 6,037,940 A | 3/2000 | Schroeder et al. .......... 345/348 |
| 6,039,688 A * | 3/2000 | Douglas et al. ............. 600/300 |
| 6,081,750 A * | 6/2000 | Hoffberg et al. ............ 700/17 |
| 6,101,500 A * | 8/2000 | Lau ............................ 707/103 |
| 6,137,499 A * | 10/2000 | Tesler ......................... 345/440 |

FOREIGN PATENT DOCUMENTS

JP 53/14150 11/1993 ........... G06F/15/21

* cited by examiner

*Primary Examiner*—Steven Sax
(74) *Attorney, Agent, or Firm*—Thelen Reid & Priest LLP; Marc S. Hanish

(57) ABSTRACT

A method and apparatus for managing changes to computerized medical protocols is provided. Each change to a medical protocol results in a new binary file being generated. Each binary file associated with the protocol then has a version number, which may be divided into two parts: a major version number and a minor version number. The default is that major changes to the medical protocol result in an incremented major number while minor changes to the medical protocol result in an incremented minor number. At assignment time, the version of the medical protocol to be assigned is assumed to be the one with the highest major number. At execution time, the version of the medical protocol to be executed is assumed to be the one with the highest minor number. This allows for the constant modification of treatment protocols without interfering with the protocols of patients already receiving treatment.

26 Claims, 10 Drawing Sheets

Sore Throat Assessment
Version 1.1

Have these symptoms appeared before?  ● Yes  ○ No

If "Yes", on what date: [ ]

How long have the symptoms been present? [0] hours

Check all applicable symptoms:

☐ Cough

☐ Difficulty swallowing

☐ Fever/Flu

☐ Plegm

---

☐ Exception   Reason [ ▼]

Forward To: [ ▼]

Message: [ ]

[Submit] [Forward] [<<Back] [Save for Later]

*FIG. 6*

APPARATUS AND METHOD FOR MANAGING CHANGES OF COMPUTERIZED MEDICAL PROTOCOLS

CROSS-REFERENCE TO RELATED APPLICATIONS

This application is a Continuation-In-Part of co-pending application Ser. No. 09/153,829, entitled "A GRAPHICAL USER INTERFACE IN A MEDICAL PROTOCOL SYSTEM HAVING TIME DELAY RULES AND A PUBLISHER'S VIEW", filed on Sep. 15, 1998 now U.S. Pat. No. 6,037,940, which was a Continuation-In-Part of application Ser. No. 08/546,212, entitled "APPARATUS AND METHOD FOR A GRAPHIC USER INTERFACE IN A MEDICAL PROTOCOL SYSTEM", filed on Oct. 20, 1995 now U.S. Pat. No. 5,850,221, and application Ser. No. 08/546,213, entitled "AN APPARATUS AND METHOD FOR MERGING MEDICAL PROTOCOLS", filed on Oct. 20, 1995 now U.S. Pat. No. 5,826,237.

BACKGROUND OF THE INVENTION

1. Field of the Invention

The present invention relates to providing graphic medical healthcare plans or protocols, and in particular a graphic user interface, for managing changes of such protocols.

2. The Background

Typically, developing a healthcare plan for providing medical services to patients has been a manual exercise. This process is fraught with inefficiencies related to sharing of information, data accuracy, and capturing complexity. Computerization of healthcare plans alleviates these problems and permits a new set of behaviors that would be prohibitive (or even impossible) in a manual system. However, most computerized implementations of manual processes tend to be static in nature. Even if they include branching logic for alternate process paths, the logic is codified a priori, in that changes to the process require wholesale application. That is, all patients in a system must use a given plan as it was originally designed. New versions of the plan are immediately applied to all patients in a system (past, present, or future).

However, treatment plans often change over time. Doctors may discover newer ways to treat certain ailments or they may simply decide that certain diagnosis or treatment decisions should be altered to be made more effective. This may result in multiple "versions" of the same treatment plan. If a treatment plan is currently in use by a particular patient, major changes to the treatment plan could create chaos. For example, strep throat is generally treated with an antibiotic. If a patient was assigned this treatment and was currently on day 3 of a 12 day course of antibiotics, nothing should prevent that patient from continuing the antibiotic treatment. Even if a radically new anti-strep drug was invented, the patient should not stop the current course of antibiotics. Thus, while new patients developing strep throat should receive the new drug (as part of the new treatment plan for strep throat), existing patients should continue with the old treatment plan.

There are minor changes to treatment plans, however, that should be applied to patient currently receiving treatment under the plan, for example if new test results come in, or if old test results are deemed to be incorrect or unreliable. Thus it is desirable that an apparatus and method for providing a medical healthcare plan will also include the ability to differentiate between major and minor changes to treatment plans and to either apply a new plan or not apply a new plan to an existing patient based on the differentiation between the two types of changes.

Furthermore, when such an ability exists, the result may be multiple instances of the same treatment plan being available at any one period of time. As time goes by, physicians may choose to eliminate certain instances of the treatment plan, merge them with the most recent plan, or even create new plans combining the best aspects of prior treatment plans. It is therefore desirable that an apparatus and method for providing a medical healthcare plan will also include the ability to manage multiple versions of the treatment plans.

SUMMARY OF THE INVENTION

A method and apparatus for managing changes to computerized medical protocols is provided. Each change to a medical protocol results in a new binary file being generated. Each binary file associated with the protocol then has a version number, which may be divided into two parts: a major version number and a minor version number. The default is that major changes to the medical protocol result in an incremented major number while minor changes to the medical protocol result in an incremented minor number. At assignment time, the version of the medical protocol to be assigned is assumed to be the one with the highest major number. At execution time, the version of the medical protocol to be executed is assumed to be the one with the highest minor number. This allows for the constant modification of treatment protocols without interfering with the protocols of patients already receiving treatment.

BRIEF DESCRIPTION OF THE DRAWINGS

FIG. 6 is a diagram illustrating version 1.1 of an order for completion according to the present invention.

DETAILED DESCRIPTION OF A PREFERRED EMBODIMENT

I. OVERVIEW

A. Software and Hardware Environment

The term "template" is used to refer to a generic healthcare treatment plan, protocol, or guideline. After a template has been assigned to a general patient or client, the template is referred to as "plan".

Those of ordinary skill in the art will realize that the following description of the present invention is illustrative only and not in any way limiting. Other embodiments of the invention will readily suggest themselves to such skilled persons after review of this disclosure.

In accordance with a presently preferred embodiment of the present invention, the components, processes and/or data structures are implemented using C++ and stored on a computer readable medium. Different implementations may be used and may include other types of programming languages, computing platforms, computer programs, firmware and/or general purpose machines. In addition, those of ordinary skill in the art will readily recognize that devices of a less general purpose nature, such as hardwired devices, devices relying on FPGA (field programmable gate array) or ASIC (Application Specific Integrated Circuit) technology, or the like, may also be used without departing from the scope and spirit of the inventive concepts disclosed herein.

The software or computer readable program code, according to one embodiment, used in developing, displaying and implementing templates and healthcare treatment plans, is named ConferWeb™. In a preferred embodiment, ConferWeb™ software is stored on a computer readable medium. In the preferred embodiment, ConferWeb™ software program would be used in conjunction with a computer system having the following requirements. The computer is an International Business Machine™ ("IBM") compatible computer having a 386, 486, Pentium™, Pentium™ II, or Pentium™ III processor. The operating system may be a Microsoft™ Windows™ 3.1, Windows™ 3.11, Windows™ 95, Windows™ 98 or Windows™ NT operating system. The minimum random access memory ("RAM") would be 8 megabytes ("MB") and preferably 16 MB. For relatively small RAM systems, virtual memory must be set as high as possible. In an embodiment, virtual memory must be set to a minimum of 12 MB. In the preferred embodiment, ConferWeb™ program would operate in conjunction with Microsoft Foundation Class ("MFC") software files and with WIN 32s software files in a 16-bit environment. Available hard disk drive space should include 2 to 7 megabytes depending on the size of the data and whether or not MFC or WIN 32s system files are being used. The monitor would preferably be a video graphic adapter ("VGA") or super video graphic adapter ("SVGA") color monitor.

In the preferred embodiment, the computer system would have an input/output device, such as a mouse, for "clicking" graphic elements. Clicking graphic elements refers to positioning a cursor on a display, which is controllable by the mouse, on or near a graphic element and pushing a mouse button.

B. Graphic User Interface Overview

1. TEMPLATE CREATION

Figure 1:
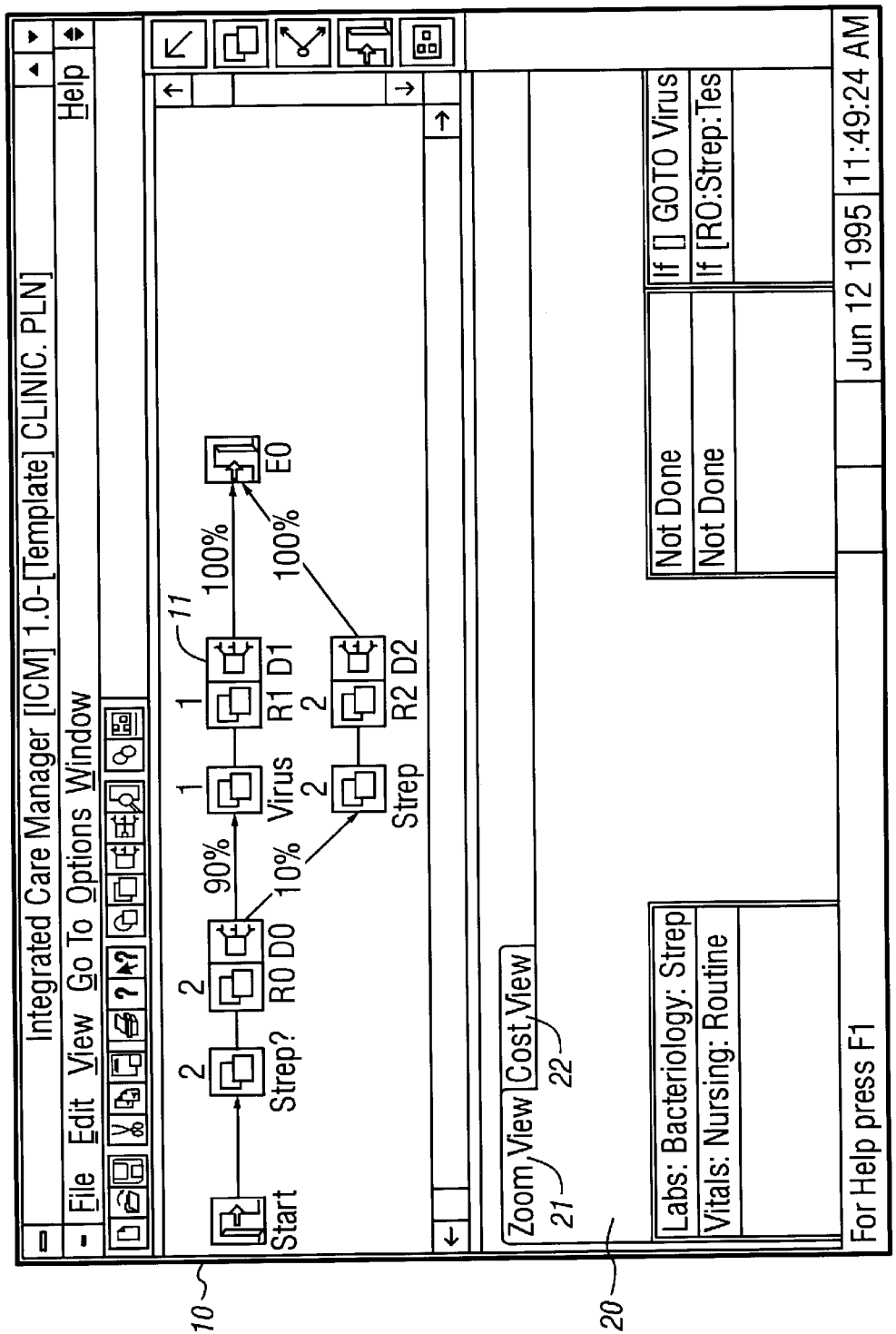
FIG. 1 is a diagram illustrating an example of a Template Builder window with an open template according to the present invention.

FIG. 1 is a diagram illustrating an example of a Template Builder window with an open template. The template graphically represents a medical healthcare treatment plan in upper window 10. The upper window 10 shows a Flow Chart view 11 of a medical healthcare treatment plan. The template contains a number of graphic elements including: a start node, three triplets of an order node, a result node, a flow control node and an exit node. These graphical elements are positioned in window 10 in order to represent a medical healthcare treatment plan.

In Flow Chart view 11, the process flow begins with a Start node, enters into the first Order nodes, and flows out to Result nodes. After the results are entered, the process flow continues on to a Flow Control node where the next step in the treatment is determined.

The bottom viewing window 20 contains two different views of the template, each on separate tabs: Zoom view 21 and Cost view 22. A user flips between these views by clicking the corresponding tab. A user can also choose Zoom view and Cost view options from a View menu to show a specific template view.

The Zoom view is used to see the details inside the nodes of the template. Each node is magnified or expanded to show information contained within, as well as the relationships between the nodes in the flow chart. A user can use this view to examine the entire template.

The Template Builder tool is used to create and modify templates. When saving changes after modifying an existing template, the user is prompted for versioning information. The user classifies their changes as either minor or major. The tool may provide an initial default classification based on an analysis of the changes the user made. The tool then passes the entered classification on to the versioning system as described in detail below.

2. ASSIGNING A TEMPLATE TO A PATIENT

A template may be assigned to one or more patients. When a template is assigned to a patient, it becomes part of the patient's plan. The patient's plan is a collection of all of the templates that have been assigned and possibly tailored to the specific patient. Once a template is assigned to a patient, the template may be modified or executed.

Figure 2:
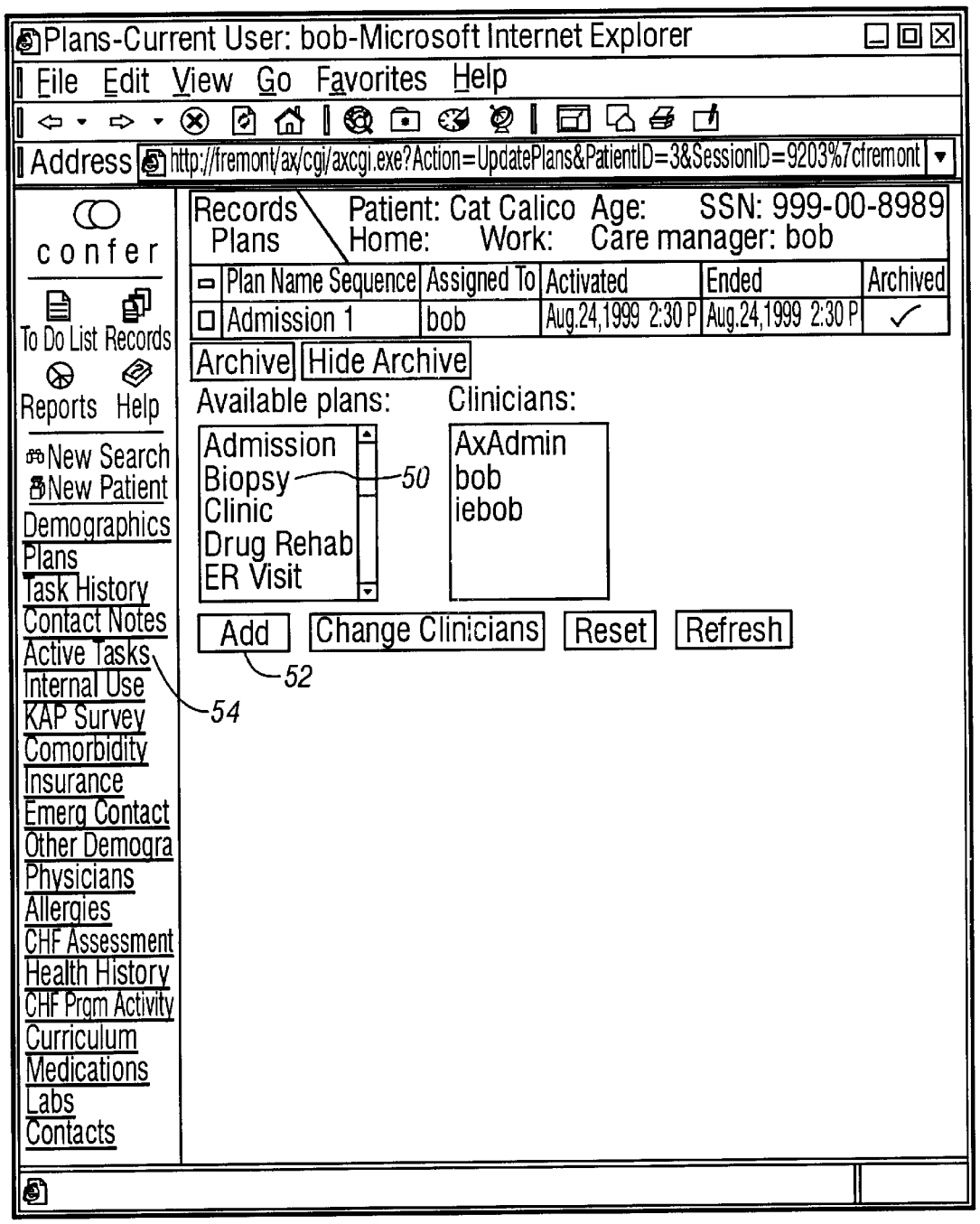
FIG. 2 is a diagram illustrating a Patient Search Page used to retrieve a patient for template assignment according to the present invention.
Figure 3:
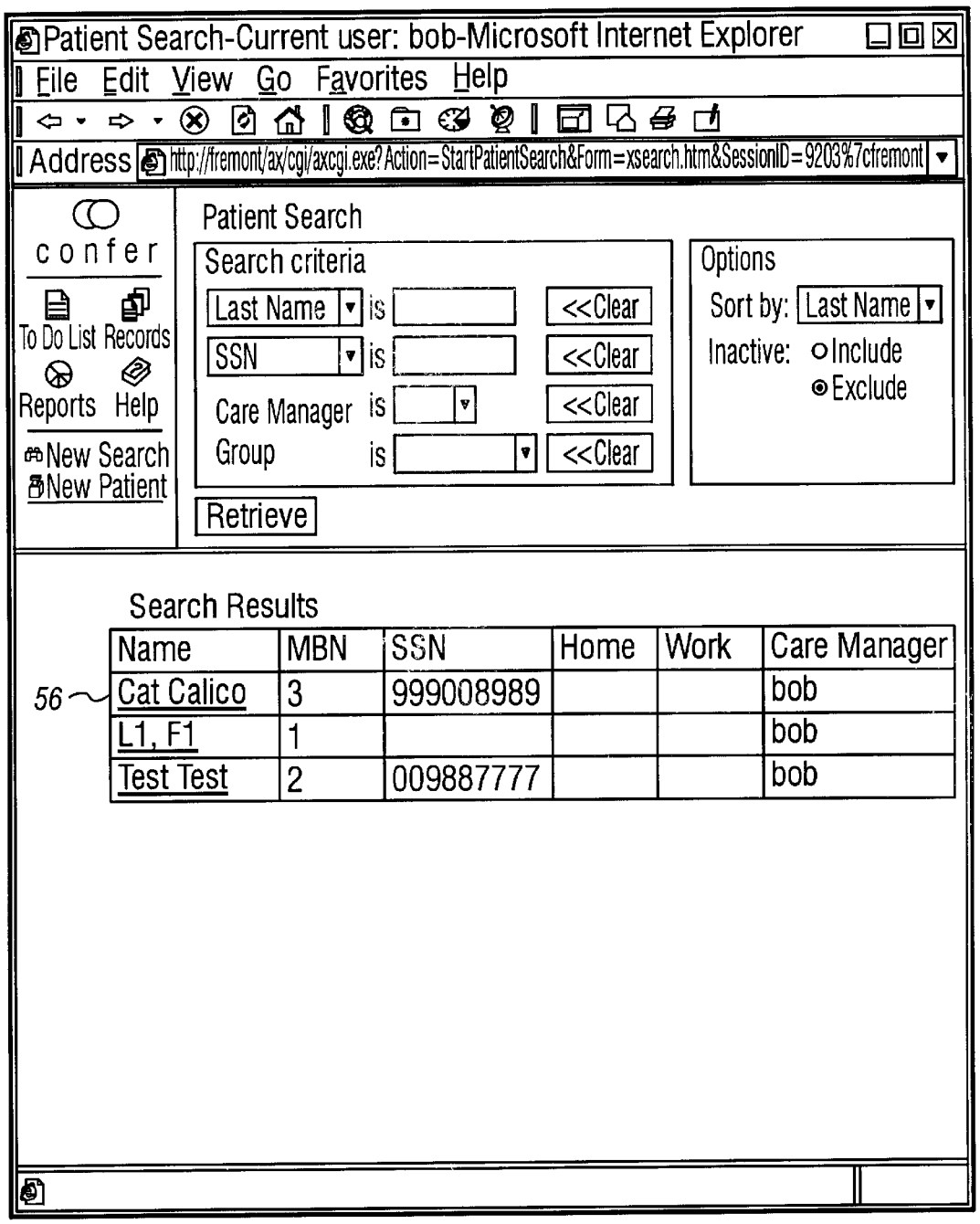
FIG. 3 is a diagram illustrating the Plan Assignment Page according to the present invention.

To assign the Clinic template to a patient:

a. Identify the patient via a search mechanism as shown in FIG. 2. Select the patient by clicking on the patient hyperlink 56. The plan assignment page is displayed as shown in FIG. 3.

b. Click the template name 50 to select the template.

c. Click Add 52, which assigns the template. The patient assignment is recorded.

3. PATIENT CHARTING

A template assigned to a patient becomes part of the patient's plan and can be delivered. During the delivery operations, a user enters the results of tests and changes the status of orders when the order has been completed (i.e., filled).

Figure 4:
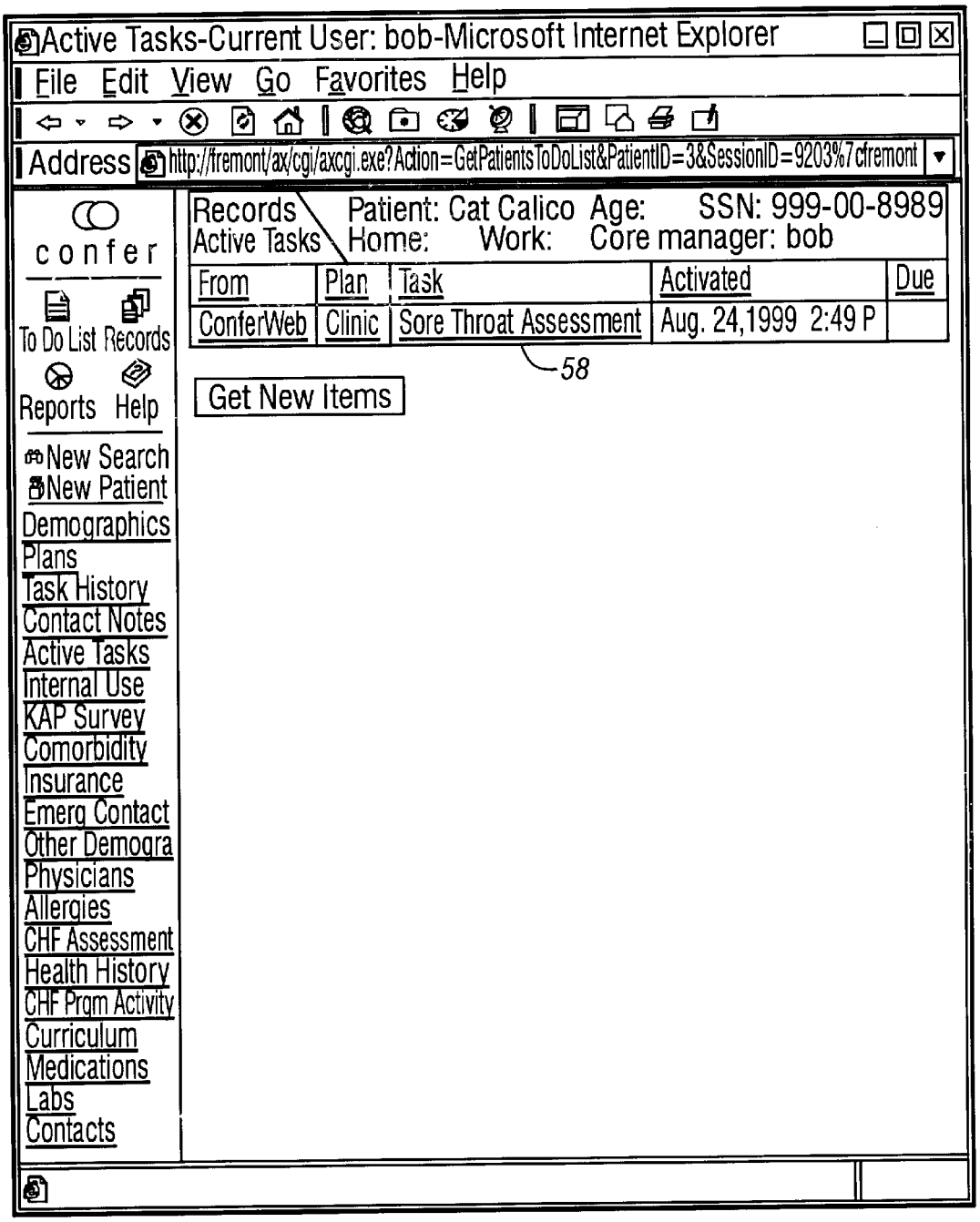
FIG. 4 is a diagram illustrating a list of orders that must be completed for a particular patient according to the present invention.
Figure 5:
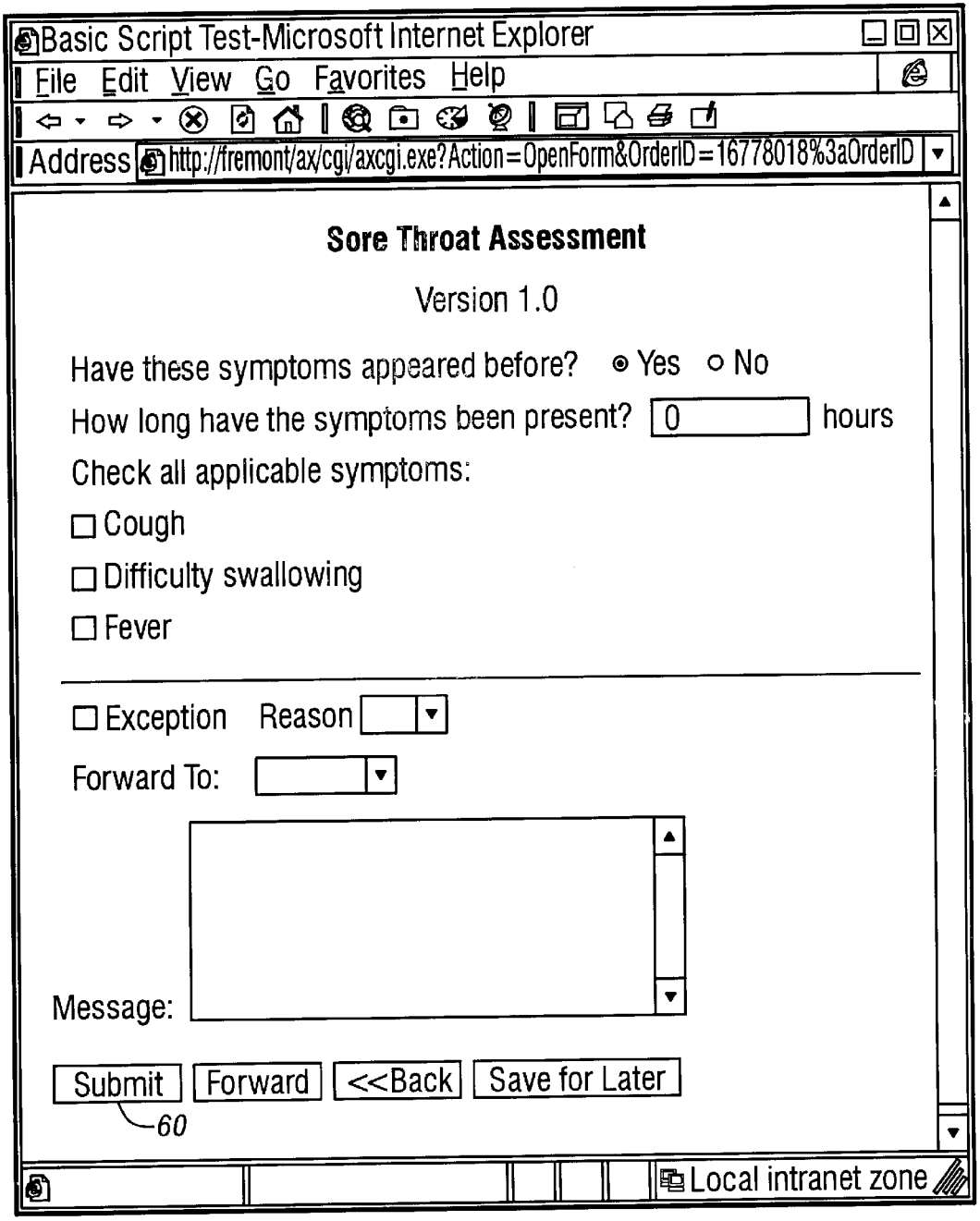
FIG. 5 is a diagram illustrating version 1.0 of an order for completion according to the present invention.

To deliver a patient's plan:

a. After assigning the template as shown in FIG. 3, click on the active tasks hyperlink 54 to navigate to a list of tasks for that patient, as shown in FIG. 4.

b. Click on an order hyperlink 58 to open the order for entering results.

c. Complete the contents of the order. FIG. 5 shows version 1.0 of an order for assessing a sore throat complaint. Submit the order contents by clicking on the submit button 60.

d. Upon order submission, the system progresses according to the appropriate template version as described below.

If during the delivery of the plan for a patient a new version of the order, version 1.1, becomes available, the template is updated with a minor version. The next time the order appears in the template for the patient, opening it will display the new version, as shown in FIG. 6.

Figure 7:
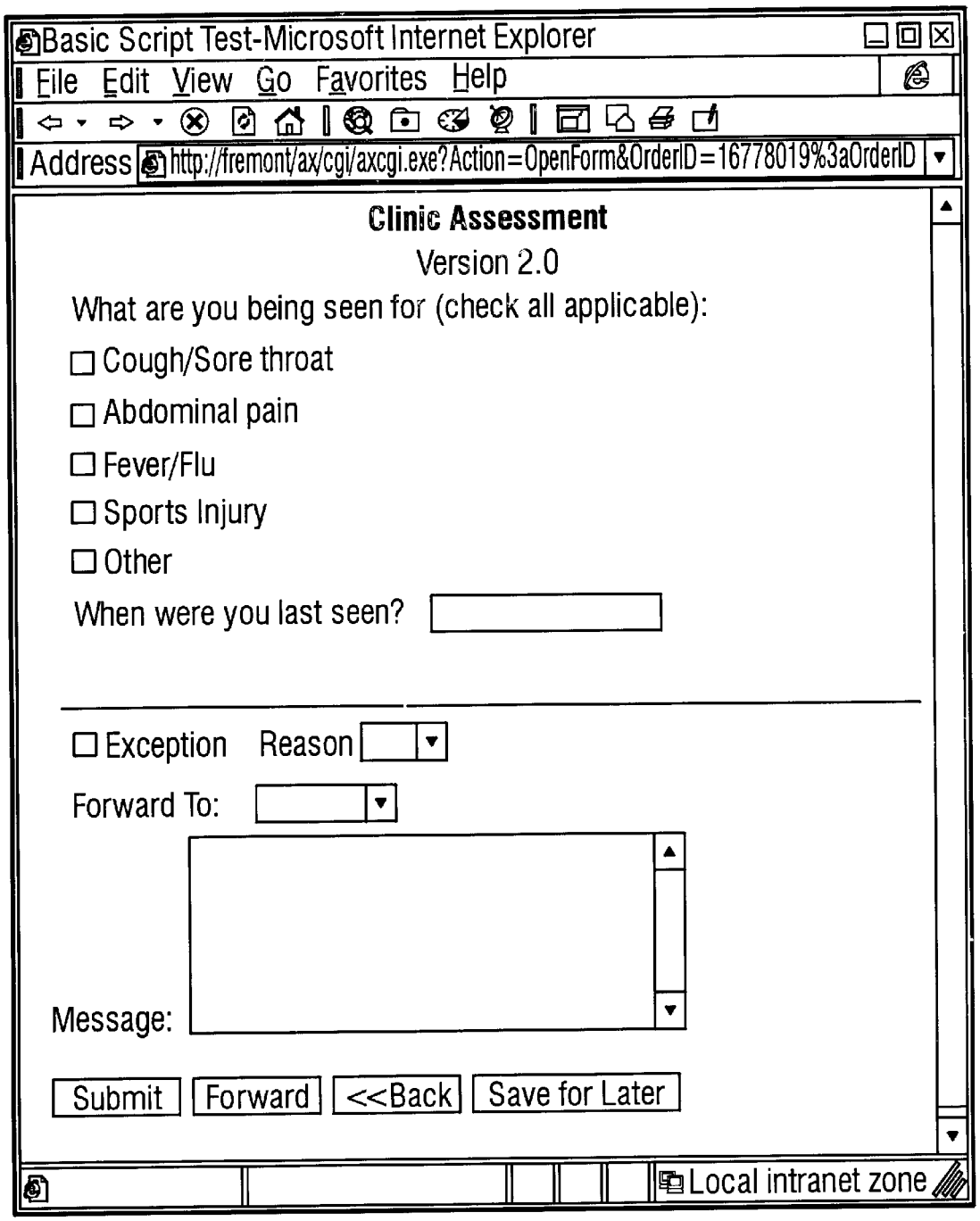
FIG. 7 is a diagram illustrating version 2.0 of an order for completion according to the present invention.

If during the delivery of the plan for a patient the template is altered so that a different order is used for the assessment, the template is updated with a major version. The plan delivery for existing patients continues as if there were no change to the template. However, new template assignments will use the latest major version, and so will get the latest order version, version 2.0, when opening orders as shown in FIG. 7.

II. MANAGING CHANGES TO PLANS

A. The Problem

It is often the case that treatment plans change over time. Doctors discover new drugs and techniques to treat patients with certain ailments all the time. Additionally, the practice of medicine is often referred to as an "art" rather than a "science" because there is little precision in how diagnoses are made. A doctor often combines book knowledge and lab and test results with his or her own experience as and "gut reaction". Thus, if a patient is not responding to a specific type of treatment, a doctor will often alter the treatment or apply an entirely new treatment in an attempt to alleviate the health problem.

Thus, when using the ConferWeb™ software, the doctor may change the treatment plan or template quite often, either to improve the treatment of a specific treatment or as a global change to the treatment plan for all patients. Therefore, a mechanism for managing such changes is provided.

B. Version Numbers

Each treatment plan or template is assigned a unique name or other identification, and then is stored as a binary file. This binary file is called a "template object". When a doctor wishes to implement a specific treatment plan for a specific patient, the template object is "assigned" to the patient. This involves basically making a copy of the object and giving this copy an identifier that allows the program to recognize that it is assigned to the specific patient. Modifications may then be made to the specific patient's template object without necessarily affecting the global template object.

While there are many modifications made to a specific patient's template object that should not be made to the global template as well (such as filling in the patient's test results, or altering the dosage of a drug due to a bad reaction), there are also some modifications that the doctor may want to apply to the global template or plan (such as if an entirely new drug for treating the ailment is invented). The differentiation between the two is made by utilizing a version number.

Each template object has a version number stored in the template description in the binary template object file. The version number is made up of two parts: a major number and a minor number, and may be read in the form <major number>.<minor number>. Thus, a template object with a major number of 4 and a minor number of 1 may be termed version 4.1 of the template object. In general, each part of the version number is read such that a higher number indicates a newer version. A change in the major number signifies a change that should be reflected in the global template, while a change in the minor number should only be reflected in the template object to which it is assigned. Thus "major" changes will change the major number, while "minor" changes will change the minor number.

While a doctor may signify whether he or she believes that the specific modification constitutes a "major" change or "minor" change by altering the version number, default rules must be in effect. Generally, any change to a form will be a minor change, while any change to any other portion of the template object (such as adding, moving, or removing nodes) will be a major change. The program then automatically creates a new version number for the template object based on what type of modification was made. This new version number can then be overridden by the doctor or other user if it is deemed appropriate.

C. Choice of Template Version at Assignment Time vs. Execution Time

Most of the time it is inappropriate to delete templates, as doctors will often try new types of treatments while still relying occasionally on treatments of the past. Since disk storage space is generally cheap and the amount of data in a template object is minor, having multiple versions of the same plan existing on the system simultaneously is not uncommon.

A challenging problem is that a major change in the preferred method of treatment may normally not be used for a patient who has already commenced treatment. Generally speaking, treatments must be substantially if not entirely completed before another treatment for that same problem is attempted. Thus, while major changes in a template should affect the global template, allowing future patients to take advantage of the new treatment, these major changes should probably not affect template objects already assigned. Again, this is something that the doctor may override as the case may warrant (for example, it is safe to interrupt a doctor's prescribed influenza treatment of "bed rest and lots of fluids" with a newly approved drug treatment).

In order to be consistent with the requirements listed above, when a plan is assigned to a patient, the program will assign the template object with the highest major number to that patient. On the other hand, when a plan is being executed, the template object used for execution will be the template object with the highest minor number of the template objects having a major number equal to the highest major number at the time of plan assignment. The following example may help to illustrate:

Several versions of a strep throat treatment plan may exist on the system, these include versions 1.0, 2.0, and 3.0. When a patient arrives complaining of a strep throat, strep throat template object 3.0 is assigned to the patient. During the course of his treatment, several minor modifications are made to his template, including filling in forms with test results, resulting in versions 3.1, 3.2, and 3.3 existing as well. Then a change in the order of certain nodes within the template object is changed as part of a new diagnostic technique is implemented. This results in a version 4.0 being created. When the patient's template is executed, the template utilized will be version 3.3, because that is the template version which has the highest minor number of templates with the same major number as the one at plan execution time (3). However, if a new patient comes in complaining of strep throat, he is assigned version 4.0, because that is the template with the highest major number.

D. Additional Features Using Template Version Numbers

The fact that version numbers are maintained for the multiple versions of templates stored on the system allows for several additional features which improve the ability to manage these multiple version.

1. Visual Comparison of Two Template Versions

Figure 8:
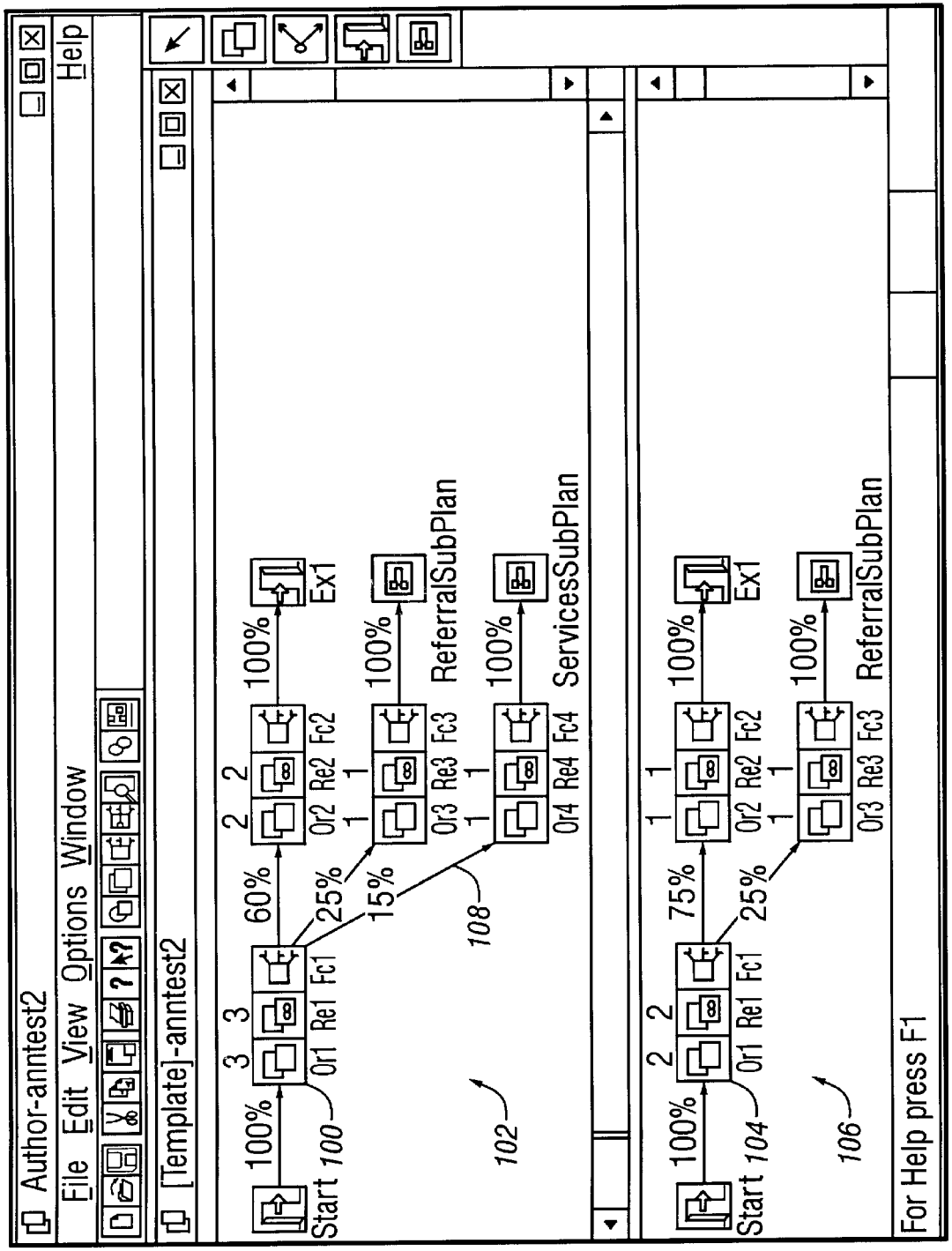
FIG. 8 is a diagram illustrating how two versions of a template may be displayed on a computer screen simultaneously.

FIG. 8 is a diagram illustrating how two versions of a template may be displayed on a computer screen simultaneously. The differences between the two version may be further marked in color to distinctly show the differences. For example, if the content of the first node 100 in the template displayed on top 102 is different from the content of the first node 104 in the template displayed on the bottom 106, the colors of the nodes may be different. Likewise, if a branch 108 exists in the template displayed on top 102 that doesn't exists in the template displayed on the bottom 106, the branch 108 may be in a color that stands out from the rest of the branches in the template. This allows the doctor or user to easily spot differences between template versions.

2. Visual Merging of Two Template Versions

Rather than displaying two templates on the screen one on top of the other, two templates may be merged visually so that they appear to lie on top of one another. Each template may be assigned a different color so that differences between the two templates may be easily recognizable.

3. Manual Identification of the Version Desired for Assignment

If the user wishes to overrule the default template that would normally be assigned at assignment time, a dialog box may allow the user to select one of the versions to assign instead.

4. List all Versions of a Plan/Template

All versions of a plan or template may be listed on the screen to allow the user to easily modify, select, delete, etc. the precise plan or plans he desires.

E. Method and Apparatus

Figure 9:
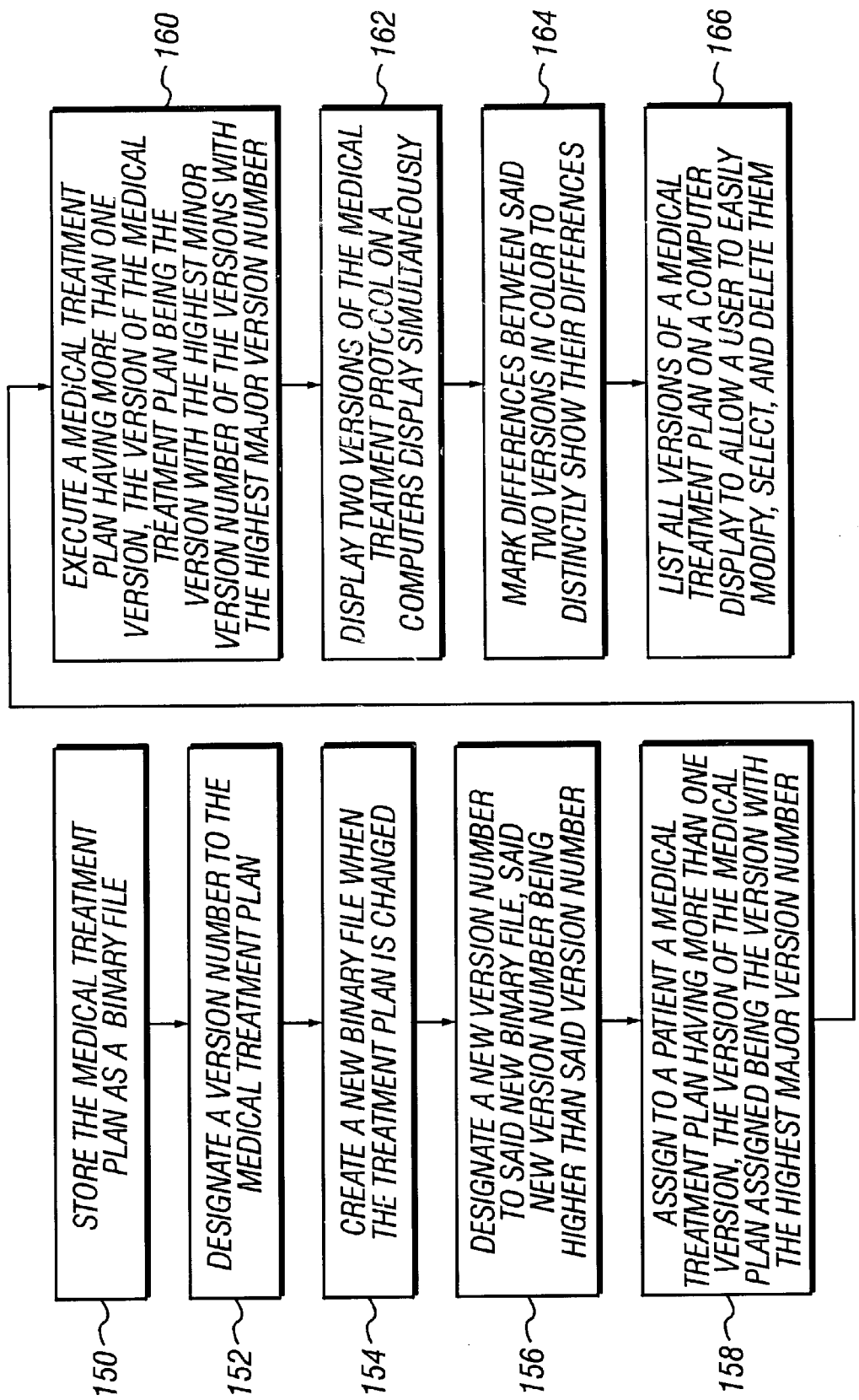
FIG. 9 is a flow diagram illustrating a method for managing a change to a medical treatment plan.

FIG. 9 is a flow diagram illustrating a method for managing a change to a medical treatment plan in accordance with a presently preferred embodiment of the present invention. At 150, the medical treatment plan is stored as a binary file. At 152, a version number is designated to the medical treatment plan. At 154, a new binary file is created when the treatment plan is changed. At 156, a new version number is designated to said new binary file, said new version number being higher than said version number. This version number, as described above, may comprise two parts: the major and the minor version number, which each represent either a major or minor change to the treatment plan. When a medical treatment plan is assigned at 158, if the plan has more than one version the version of the plan assigned will be the version with the highest major version number. When a medical treatment plan is executed at 160, if the plan has more than one version the version of the plan assigned will be the version with the highest minor version number of the versions with the highest major version number.

At 162, two versions of the medical treatment protocol may be displayed on a computer display simultaneously, and at 164 the differences between the two version may be marked in color to distinctly show their differences. At 166, all versions of a medical treatment plan may be listed on a computer display to allow a user to easily modify, select, and delete them.

Figure 10:
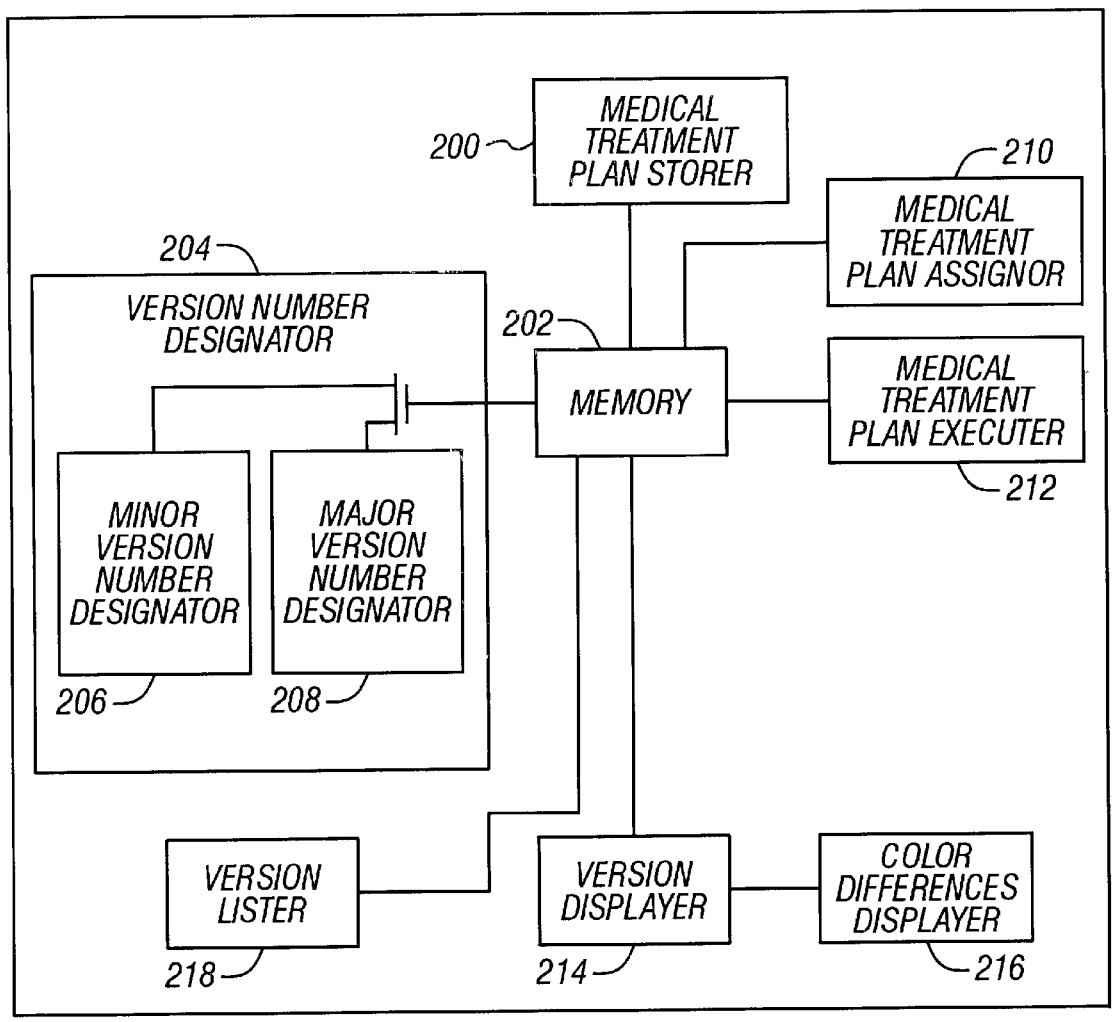
FIG. 10 is a block diagram illustrating a computer system for managing changes to a medical treatment plan.

FIG. 10 is a block diagram illustrating a computer system for managing changes to a medical treatment plan. A medical treatment plan storer 200 stores the medical treatment plan as a binary file in memory 202. A version number designator 954 designates a version number to the medical treatment plan. A new binary file is created by the medical treatment plan storer 200 when the treatment plan is changed. A new version number is designated to said new binary file by the version number designator 204, said new version number being higher than said version number. This version number, as described above, may comprise two parts: the major and the minor version number, which each represent either a major or minor change to the treatment plan. Thus, the version number designator 204 may comprise a major version number designator 206 and a minor version number designator 208, the major version number designated coupled to said memory if a major change is made to the medical treatment plan and the minor version number designator coupled to said memory if a minor change is made to the medical treatment plan. A medical treatment plan assignor 210 assigns the medical treatment plan when the plan is to be assigned. If the plan has more than one version the version of the plan assigned will be the version with the highest major version number. A medical treatment plan executor 212 executes the medical treatment plan when it is to be executed. If the plan has more than one version the version of the plan assigned will be the version with the highest minor version number of the versions with the highest major version number.

A version displayer 214 allows two versions of the medical treatment protocol to be displayed on a computer display simultaneously, and a color differences displayer 216 allows the differences between the two version may be marked in color to distinctly show their differences. A version lister 218 allows all versions of a medical treatment plan to be listed on a computer display to allow a user to easily modify, select, and delete them.

III. CONCLUSION

The foregoing description of the preferred embodiments of the present invention has been provided for the purposes of illustration and description. It is not intended to be exhaustive or to limit the invention to the precise forms disclosed. While embodiments and applications of this invention have been shown and described, it would be apparent to those skilled in the art after review of this disclosure that many more modifications than mentioned above are possible without departing from the inventive concepts herein. The invention, therefore, is not to be restricted except in the spirit of the appended claims.

We claim:

1. A method for managing a change to a medical treatment plan, wherein the medical treatment plan indicates an outline of future diagnostic tests and/or treatment options, including:

storing the medical treatment plan as a global template object, said global template object stored as a binary file;

designating a version number to the medical treatment plan;

creating a new binary file when said medical treatment plan is changed; and designating a new version number to said new binary file, said new version number being higher than said version number;

making a copy of said global template object, thus creating a specific patient template object;

designating said specific patient template object as assigned to said patient;

wherein said version number includes a major version number and a minor version number, and changing the major version number if a major change is made to the medical treatment plan and changing the minor version number if a minor change is made to the medical treatment plan, wherein a major change is one that is intended to alter said global template object and a minor change is one that is intended to alter said specific patient template object; and displaying elements of the medical treatment plan and the linkages between said elements via a user interface.

2. The method of claim 1, further including:

assigning to a patient a medical treatment plan based upon said version number of said medical treatment plan.

3. The method of claim 1, wherein said new version number has a higher major number than said version number if a major change is made to the medical treatment plan and said new version number has a higher minor number than said version number if a minor change is made to the medical treatment plan.

4. The method of claim 3, further including:

assigning to a patient a medical treatment plan having more than one version, the version of the medical treatment plan assigned being the version with the highest major version number.

5. The method of claim 3, further including:

executing a medical treatment plan having more than one version, the version of the medical treatment plan being the version with the highest minor version number of the versions with the highest major version number at the time of plan assignment.

6. The method of claim 3, wherein said medical treatment plan includes one or more forms, a minor change changes to one of said forms, and a major change changes to any other portion of said medical treatment plan.

7. The method of claim 3, wherein said medical treatment plan includes one or more forms and one or more nodes, a minor change changes to one of said forms, and a major change changes involving adding, moving, or removing nodes.

8. The method of claim 1, further including displaying two versions of the medical treatment protocol on a computer display simultaneously.

9. The method of claim 8, further including marking differences between said two versions in color to distinctly show their differences.

10. The method of claim 1, further including listing all versions of a medical treatment plan on a computer display to allow a user to easily modify, select, or delete them.

11. A computer system for managing a change to a medical treatment plan, wherein the medical treatment plan indicates an outline of future diagnostic tests and/or treatment options, including:

a memory;

a medical treatment plan storer coupled to said memory; and a version number designator coupled to said memory;

storing the medical treatment plan as a global template object, said global template object stored as a binary file;

the system making a copy of said global template object, thus creating a specific patient template object;

the system designating said specific patient template object as assigned to said patient;

wherein said version number includes a major version number and a minor version number, the version number designator changing the major version number if a major change is made to the medical treatment plan and changing the minor version number if a minor change is made to the medical treatment plan, wherein a major change is one that is intended to alter said global template object and a minor change is one that is intended to alter said specific patient template object; and the system displaying elements of the medical treatment plan and the linkages between said elements via a user interface.

12. The computer system of claim 11, further including:

a medical treatment plan assignor coupled to said memory.

13. The computer system of claim 11, wherein said version number designator includes a major version number designator and a minor version number designator and said major number designator is coupled to said memory if a major change is made to the medical treatment plan and said minor version number designator is coupled to said memory if a minor change is made to the medical treatment plan.

14. The computer system of claim 13, further including:

a medical treatment plan assigner coupled to said memory.

15. The computer system of claim 13, further including:

a medical treatment plan executor coupled to said memory.

16. The computer system of claim 13, wherein said medical treatment plan includes one or more forms, a minor change changes to one of said forms, and a major change changes to any other portion of said medical treatment plan.

17. The computer system of claim 13, wherein said medical treatment plan includes one or more forms and one or more nodes, a minor change changes to one of said forms, and a major change changes involving adding, moving, or removing nodes.

18. The computer system of claim 11, further including a version displayer coupled to said memory.

19. The computer system of claim 18, further including a color differences displayer coupled to said version displayer.

20. The computer system of claim 11, further including a version lister coupled to said memory.

21. A program storage device readable by a machine, tangibly embodying a program of instructions executable by the machine to perform a method for managing a change to a medical treatment plan, wherein the medical treatment plan indicates an outline of future diagnostic tests and/or treatment options, the method comprising:

storing the medical treatment plan as a global template object, said global template object stored as a binary file;

designating a version number to the medical treatment plan;

creating a new binary file when said medical treatment plan is changed; and designating a new version number to said new binary file, said new version number being higher than said version number;

making a copy of said global template object, thus creating a specific patient template object;

designating said specific patient template object as assigned to said patient;

wherein said version number includes a major version number and a minor version number, and changing the major version number if a major change is made to the medical treatment plan and changing the minor version number if a minor change is made to the medical treatment plan, wherein a major change is one that is intended to alter said global template object and a minor change is one that is intended to alter said specific patient template object; and displaying elements of the medical treatment plan and the linkages between said elements via a user interface.

22. The method of claim 1, wherein said new version number has a higher major number than said version number if a major change is made to the medical treatment plan and said new version number has a higher minor number than said version number if a minor change is made to the medical treatment plan.

23. A method for managing a change to a medical treatment plan, including:

storing the medical treatment plan as a global template object, said global template object containing a start node representing the beginning of the medical treatment plan, one or more order nodes representing medical treatment options, and an exit node, said global template object stored as a binary file;

designating a version identification to the medical treatment plan;

creating a new binary file containing as a global template object when said medical treatment plan is changed; and designating a new version identification to said new binary file;

making a copy of said global template object, thus creating a specific patient template object;

designating said specific patient template object as assigned to said patient;

wherein said version identification includes a major version number and a minor version number, and changing the major version number if a major change is made to the medical treatment plan and changing the minor version number if a minor change is made to the medical treatment plan, wherein a major change is one that is intended to alter said global template object and a minor change is one that is intended to alter said specific patient template object; and displaying elements and said nodes of the medical treatment plan and the linkages between said elements and said nodes via a user interface.

24. The method of claim 23, wherein said one or more order nodes each comprise:

a first order node, said first order node indicating an action to be taken in medically treating a patient;

a result node, said result node indicating an outcome for said action indicated in said first order node; and a flow control node, said flow control node pointing to either another of said order nodes or to said exist node, said flow control node indicating a next step in medically a patient.

25. The method of claim 24, wherein said result node is initially empty and is, filled in after said action to be taken is actually taken.

26. The method of claim 25, wherein which of said another of said order nodes that said flow control node points to may be altered by information contained in said filled-in result node.

* * * * *